United States Patent [19]
Lees

[11] 4,250,895
[45] Feb. 17, 1981

[54] PERIODONTAL PROBE

[75] Inventor: Sidney Lees, Newton, Mass.

[73] Assignee: Forsyth Dental Infirmary for Children, Boston, Mass.

[21] Appl. No.: 23,401

[22] Filed: Mar. 23, 1979

[51] Int. Cl.³ .................... A61B 5/10; A61C 19/04
[52] U.S. Cl. ........................... 128/776; 33/174 D; 433/72
[58] Field of Search ............ 128/774, 776; 33/174 D; 73/37.5; 433/72, 102

[56] References Cited

U.S. PATENT DOCUMENTS 3,943,914  3/1976  Grenfell et al. .................. 128/776

FOREIGN PATENT DOCUMENTS 7703431  10/1978  Netherlands ........................... 433/72

OTHER PUBLICATIONS

Vitek et al., "Development of . . . probing instrument", J. Periodontal Res., 14:93-94, 1979.
Gabathuler et al., "A Pressure-Sensitive Periodontal Probe", Helv. Odont., vol. 15, pp. 114-117, Oct. 1971.
Velden et al., "Introduction . . . pressure probe", J. Clinical Periodontology, 1978:5:188-197.

*Primary Examiner*—Lee S. Cohen
*Attorney, Agent, or Firm*—Richard P. Crowley

[57] ABSTRACT

An improved periodontal probe to determine accurately the bottom wall surface of periodontal pockets by employing the controlled and monitored flow of gas from the tip of the probe and for permitting a calculation of the depth of the pocket by employing a controlled, slidable movement of the probe and measuring displacement of the probe.

21 Claims, 6 Drawing Figures

PERIODONTAL PROBE

BACKGROUND OF THE INVENTION

In the diagnosis and treatment of periodontal disease, a dentist typically will insert a probe into the gingival sulcus or periodontal pocket which surrounds a tooth, in an attempt to determine the depth of the periodontal pocket. Traditionally, the depth is determined through the mechanical sensing of the dentist as the probe tip touches the bottom wall surface of the pocket. In practice, it can be most difficult to determine the particular depth of the periodontal pocket and the bottom of the wall surface, when the tissue is diseased. A healthy gingiva has sufficient collageneous tissue at the bottom surface to resist penetration and, therefore, allow the depth to be determined easily by mechanical feel. However, where the periodontal pocket comprises diseased tissue, then the soft tissue may not resist penetration, and it can be penetrated easily by the tip of the probe without sufficient mechanical feel, to enable the dentist to determine the depth of the periodontal pocket. Therefore, it is most desirable to obtain an apparatus and a method by which the dentist or other examiners may determine accurately the depth of a periodontal pocket in the oral cavity of a patient.

In recent years, there has been a number of attempts to improve on the traditional periodontal probe. Gabathuler (15 *Helv. Odont. Acta* 114; 1971) has disclosed a pressure-sensitive probe, utilizing a piezoelectric crystal to determine the transcient forces applied during probing. While the Gabathuler probe allows more constant application of probing force, it does not improve upon the state-of-the-art technique of determining the bottom surface by mechanical feel and continues to rely on the user to apply manually the probing force.

Van der Velden (5 *Journal of Clinical Periodontology* 188; 1978) has disclosed a different type of pressure probe consisting of a plunger assembly connected to a variable air-pressure system. During probing, the plunger will intrude from the position of maximum extrusion only as the probing force exceeds the predetermined air pressure acting on the plunger. The distance at which the plunger is intruded can be read on a scale within the handle of the probe. While the van der Velden probe may allow for more accurate readings of pocket depth, it continues to rely on manual application of probing forces and does not overcome the problem of determining the bottom surface of the pocket, when the gingiva is soft or diseased.

Another periodontal probe system has been described in "Development of a Force Controlled Periodontal Probing Instrument", R. M. Vitek et al, *J. Periodontal Research* 14 93–94, 1979), wherein the probe instrument is moved by employing a spring-controlled system, but such a system does not include an end-point-indicating means.

Therefore, it is an object of my invention to provide a more accurate determination of pocket depth, even when the collageneous tissue of the pocket has deteriorated. It also is an object of my invention to provide a more constant application of probing force than can be applied ordinarily by manually held probes. Further, it is an object of my invention to provide means for mechanical or electrical determination of probe penetration to replace the traditional method of estimating the depth of penetration from visual observations. Additional objects and advantages of my invention will become apparent from the detailed disclosure that follows. It should be apparent that my invention may be utilized with appropriate modifications by those persons skilled in endodontistry for other applications, such as determining the depth of caries, root canals and fistulae.

SUMMARY OF THE INVENTION

My invention relates to an apparatus and a system for determining the depth of a periodontal pocket in the oral cavity of a patient and a method of determining such depth. In particular, one aspect of my invention concerns an apparatus and a method which employs the controlled and monitored flow of a fluid to determine the depth of a periodontal pocket. Another aspect of my invention relates to the force-controlled penetration of a pocket by a slidably movable probe, utilizing a piston and a fluid-filled cylinder, coupled with a reversible, external, driving means. In the preferred apparatus and method of my invention, a system is provided for both the force-controlled determination of the depth of a periodontal pocket, through a slidable, mounted, periodontal probe, and the determination of the bottom wall depth of the pocket by monitoring the flow of a gas from the probe. My apparatus and method provide a means of determining rapidly and accurately and displaying the depth of periodontal pockets, free from many of the errors that have traditionally hampered periodontists.

My invention, to determine the bottom wall surface of a periodontal pocket, comprises flowing a fluid, such as a gas or a liquid, through a passageway at a constant pressure and monitoring the flow rate as the passageway approaches the bottom wall surface of the pocket. Typically, the passageway is placed at one end of a periodontal probe, and the probe tip, with the exit port or passageway through which the fluid flows, is lowered into the pocket. When the passageway is unimpeded, the fluid flow will be at a constant or defined flow rate, but, as the probe tip approaches close to and contacts the bottom wall surface of the pocket, the flow rate will rapidly diminish to a different and much lesser rate, and, on contact, will be impeded and the flow rate will become essentially zero. Monitoring of the fluid-flow rate, as the probe tip approaches and contacts the bottom of the pocket, thereby provides an easy, rapid and accurate determination of the depth of the pocket, without relying on mechanical sensing by the dentist.

For example, tests have been carried out using a hypodermic needle, modified syringe and a Gilmont rotameter-type flow meter. With a gas flow of 260 ml/minute at about 20 to 25 psig, the needle tip was lowered toward a bottom surface. As the needle approached the surface, a rapid gas-flow drop to 30 ml/minute was observed, when the displacement was less than 0.1 mm. Other tests were conducted to simulate the effect that the gingival pocket sidewalls would have on the gas flow, and, from these tests, it was concluded that, while some drop in flow could be anticipated because of the constriction of the walls, it would not be greater and would not mask the rapid drop in flow rate observed, when the probe tip approached a bottom surface directly perpendicular to its line of motion.

The fluid employed to determine the end point; that is, the contact or substantial contact of the bottom surface of the pocket, may comprise a liquid, such as water or a saline solution, or preferably a gas, such as a nontoxic gas like nitrogen, helium, oxides of nitrogen, air or mixtures thereof. The use of a gas, such as air, is desirable, since air is readily available in dentists' offices and does not require disposal when used in the oral cavity.

My invention also comprises force-controlled probing of the pocket depth, employing a slidably mounted periodontal apparatus, particularly employing a hydraulic-force means or other means, which slidably moves a periodontal probe into a pocket, with a controlled external force and means to determine the depth of the pocket.

For example, in one embodiment, two cylinder-piston assemblies are fluidly connected and contain an essentially incompressible, and preferably low-viscosity, fluid. The smaller cylinder-piston assembly is inserted in the oral cavity, and the probe, which is attached to this internal piston, is displaced at the desired distance by a relatively small, controlled displacement of the larger external piston.

The controlled force to move the probe may be generated by any one of a number of means. The probing force is controlled by an external force, such as a force applied to the external piston. With well-lubricated pistons, the probing force may be made as small as desired, and certainly small gram-weight forces are practical and usable. A pressure-gauge and safety-valve system can be incorporated in the hydraulic system, to guard against over-application of the controlled probing force.

The displacement of the external piston may be used as an indicator of the depth traveled by the probe, since the relationship between these two motions depends on the ratio of the areas of the respective piston heads. The displacement of the external piston may be measured by any device which mechanically amplifies or electrically transduces the small displacement, so as to allow easy monitoring. Through proper calibration, the displacement of the probe can be read directly from an appropriate display panel.

In the preferred embodiment of my invention as hereinafter illustrated, both aspects, end-point determination by flow monitoring and controlled probing, are employed in combination. End-point determination by a flow meter can be made while the dentist manually controls the probe, and, likewise, force-controlled probing can be conducted in conjunction with other forms of determining the end point, such as pressure-sensitive means, liked piezoelectric crystals.

My invention allows a dentist or other user to apply a continuous, monitored and controlled probing force to a periodontal pocket and to determine accurately the depth of the pocket, without reliance on tactile senses. The end point and the depth traveled may be displayed visually to free the user's hands for other tasks. The patient is protected from electrical currents because the end point is determined and the displacement is monitored externally, without requiring electrical currents to flow through the oral cavity. The remote-sensing system also permits easy sterilization of the periodontal-probe assembly, without danger to the electrical components. Other advantages will become apparent to the reader or the user.

For the purpose of illustration only, my invention will be described in connection with its preferred embodiment; however, it is recognized that various changes and modifications may be made by those persons skilled in the art, all within the spirit and scope of my invention.

DESCRIPTION OF THE EMBODIMENTS

Figure 1:
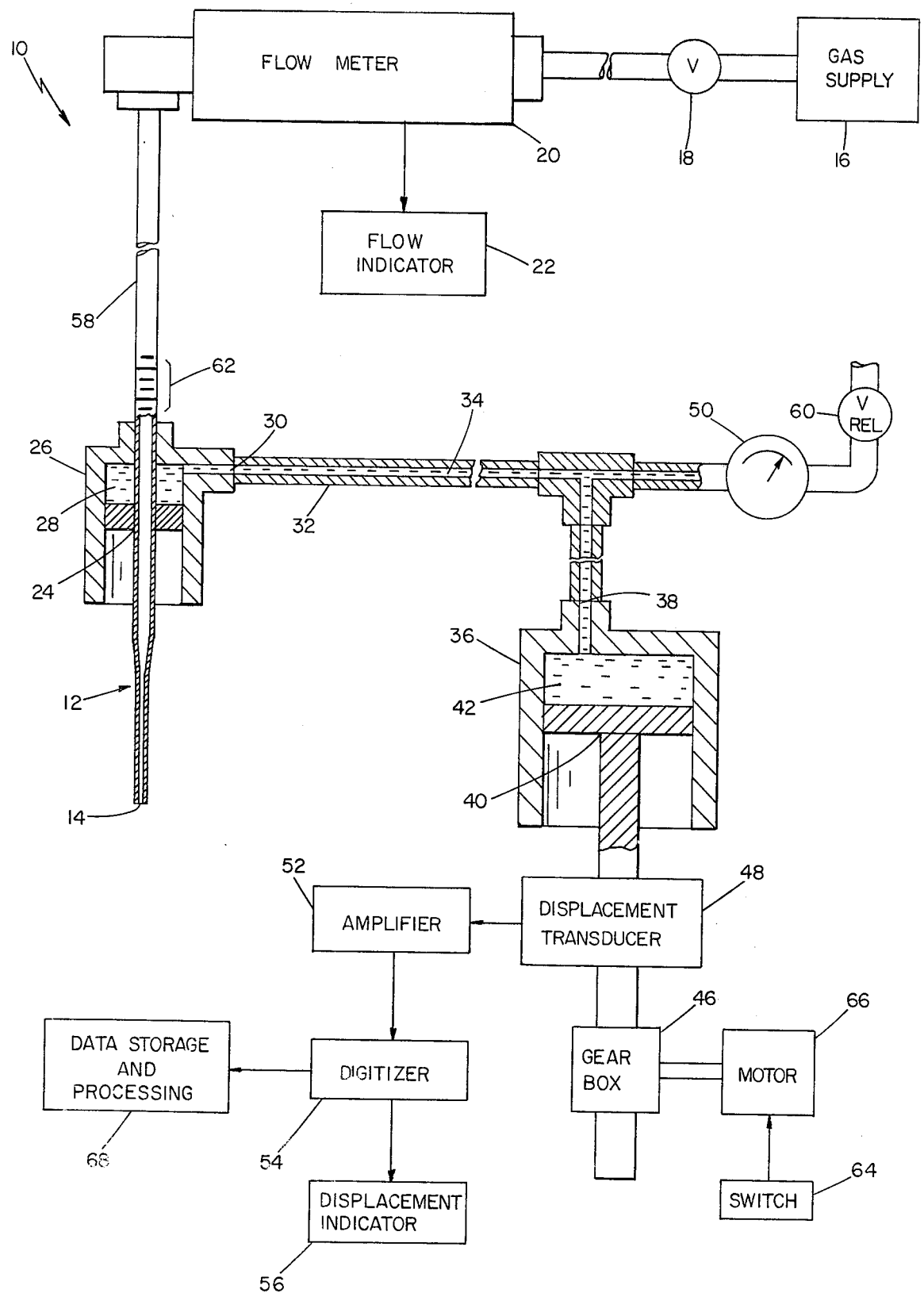
FIG. 1 is a diagramatic illustration of my invention.

Referring to the diagram of FIG. 1, there is shown the periodontal-probe apparatus 10 of this invention. The apparatus includes a periodontal probe tip 12 having an elongated, smooth body typical of probes used to explore periodontal pockets. The probe tip 12 is hollow, so as to allow passage of an inert gas through the probe tip and out an exit port 14 at the end of the probe tip. The body of the probe tip 12 is slidably mounted, so as to form an internal piston 24 which is received into an internal cylinder 26. The hollow probe tip 12 is connected to a supply of inert gas 16, such as air, by means of a gas-coupling line 58. The gas line 58 is provided with a valve 18 to regulate the gas supply. A flow meter 20 is also provided on the gas line 58, and preferably the flow meter is linked with a remote-flow indicator. Optionally, graduations 62 on the probe also may be provided for visual monitoring by the dentist of probe descent into the pocket.

FIG. 1 also shows a means for slidably moving the probe in a controlled manner into and out of the periodontal pocket. An inner cylinder 26 contains a reservoir 28 above the piston 24, which reservoir is filled with a variable volume of essentially incompressible liquid 34. The volume of fluid in the inner reservoir 28 may be varied by a number of external means. In the preferred embodiment, the fluid in the inner reservoir is coupled with an external fluid-filled reservoir 42 formed in an external cylinder 36 and piston 40. The two fluid reservoirs are connected by a flexible tube 32, with the fluid 34 entering or exiting the internal and external reservoirs by openings 30 and 38 in the internal and external cylinders, respectively. In the system, a pressure gauge 50 of standard construction is used to monitor the applied hydraulic force, and a safety-relief valve 60 also is incorporated into the fluid system.

The force applied to displace the external piston can be generated pneumatically, hydraulically, manually or electrically. The external piston 40 is driven by a reversible, electric-force generator, such as a motor 66 and gear train 46 or a solenoid. The motor 66 is controlled by a three-position switch 64 (off, forward and reverse). The motion of the external piston is measured by a linear, differential, displacement transducer 48 of adequate sensitivity and range. Alternatively, the motion can be magnified by a gear train and used to drive an angular potentiometer. The electrical output of the transducer 48, or alternatively the potentiometer, is magnified by an amplifier 52 and is converted to a digital signal by a digitizer 54. The output of the digitizer 54 is converted into a visual display by the readout indicator 56 and is fed into a data-storage and -processing unit 68.

In operation, the periodontal probe tip 12 and gas-flow meter 20, together with the adjunct valve 18, gas line 58 and indicator 22, may be used separately to determine the depth of the periodontal pocket. In such operation, the dentist maneuvers the probe tip by hand and inserts the probe-tip end into the gingival pocket and visually estimates the probe's penetration. The flow meter 20 serves to measure changes in gas transport that are caused by obstruction of the passageway of the probe tip 12. The flow meter 20 may be one of standard design, such as the Gilmont rotameter, and the flow indicator 22 likewise is of standard construction.

Figure 2:
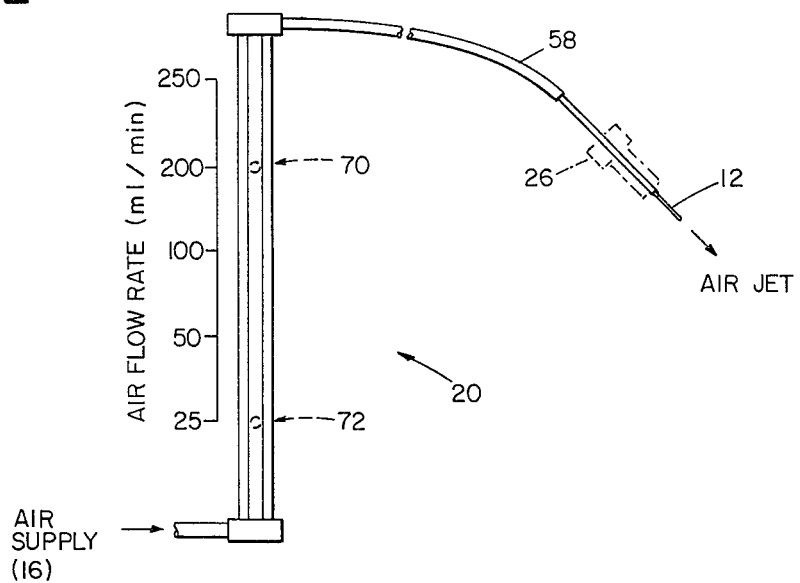
FIG. 2 is a simplified illustration of a flow meter and indicator useful with the disclosed invention.
Figure 3:
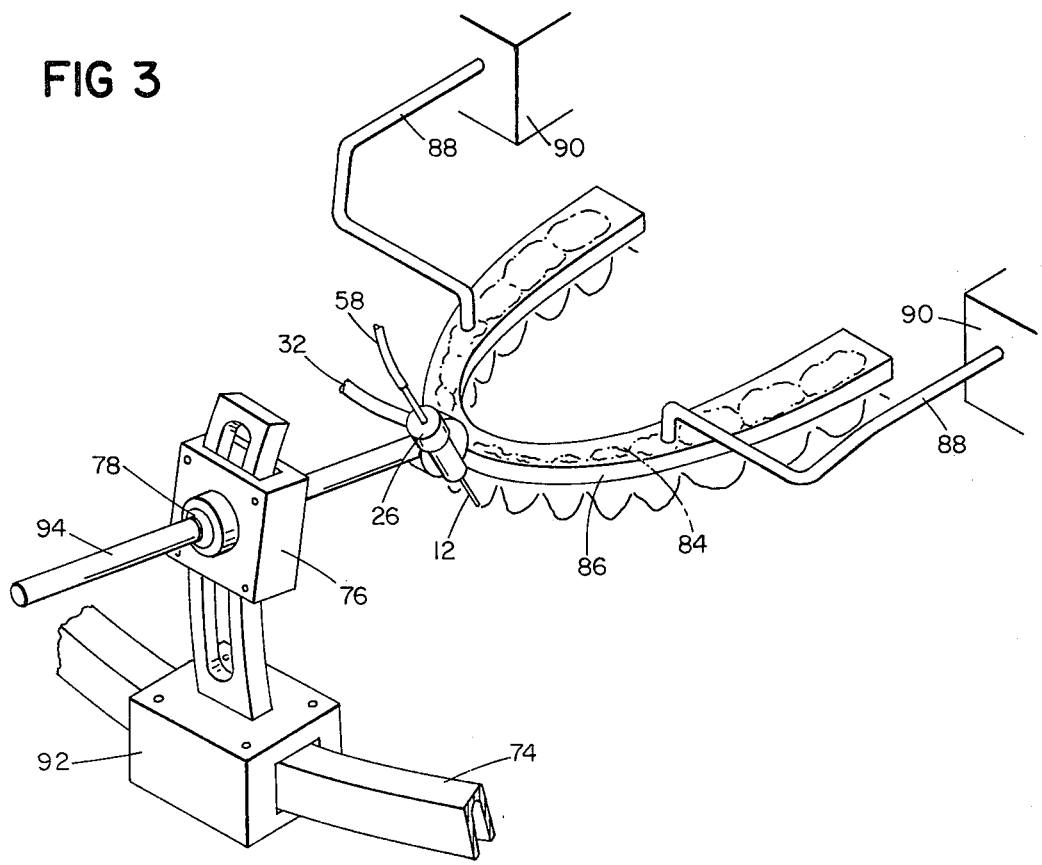
FIG. 3 is an illustration of the periodontal-probe system of this invention in the oral cavity with mechanical supports.
Figure 4:
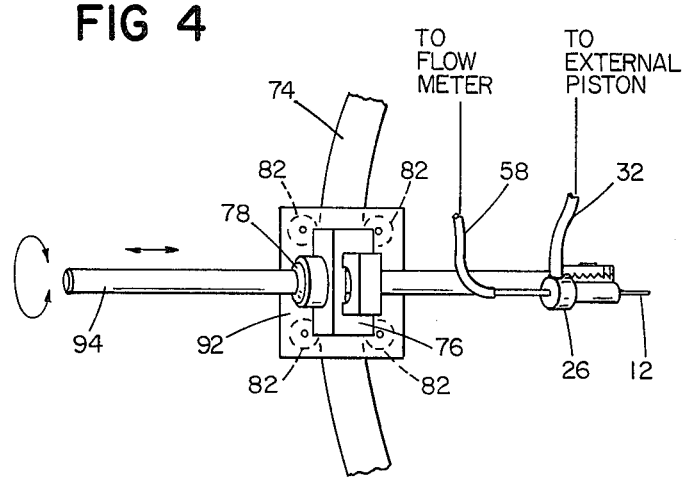
FIG. 4 is a top view of the periodontal-probe system of FIG. 3 with guided mechanical supports.
Figure 5:
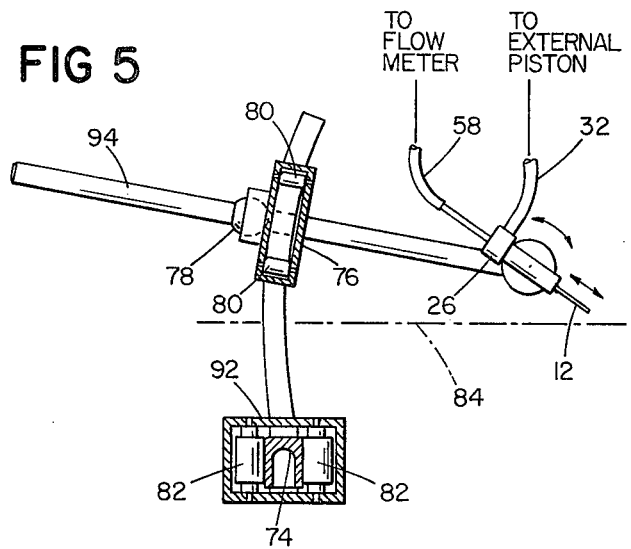
FIG. 5 is a side view of the system and guided mechanical supports, showing a sectional view of the guide-rail carriage taken along line A—A of FIG. 4.

FIG. 2 shows a simplified illustration of a flow meter and indicator useful in the practice of the invention. In FIG. 2, the position 70 is the indicator position when air flows, and the position 72 is the indicator position when airflow is blocked. When the probe is inserted into the gingival pocket, a slight drop in airflow will be registered via the flow meter 20 on the indicator 22. When the probe exit port touches the bottom wall of the pocket, a rapid drop in airflow will become apparent. The flow meter is preferably located so as to provide the user with an easily readable monitor of flow obstructions.

When used in conjunction with the hydraulic means for force-controlled application, the periodontal probe 10 is shaped so as to form an internal piston 24 capable of reciprocal, slidable movement within an internal cylinder 26, which cylinder is mounted or held securely in the oral cavity. Since the internal cylinder 26 is connected to an external supply of fluid via cylinder opening 30, the piston-shaped probe may be forced down by increasing the volume of fluid in the inner reservoir 28 and similarly may be forced up by evacuating the reservoir.

The hydraulic system shown couples the internal piston-cylinder assembly with another piston 40 and cylinder 36, which are remote or external to the oral cavity. The external piston can be displaced by any of several means. It can be done manually, with the pressure being monitored by a line-pressure gauge 50. It can be displaced by air or liquid from an external source through a valve controlled by the operator. The pressure can be regulated and limited by a safety valve 60. It can be driven electrically, either by a solenoid or by a motor through a gear train.

By suitable design, all of these means can be made reversible. My invention may be modified to include an automated feedback loop, whereby the probe can be lowered hydraulically to the bottom of the pocket, until the end point is reached. A signal from the flow indicator 22 would then reverse the external driving means and withdraw the probe. With appropriate design changes (not shown in FIG. 1), a feedback system, as described above, would permit the periodontal probe to trace out the bottom of the pocket around an entire tooth, either automatically or under manual guidance.

The movement of the internal piston 24 is proportional to the movement of the external piston 40. Thus a properly calibrated device, measuring the movement of the external piston 40 or drive rod, can be used to calculate the depth traveled by the periodontal probe. In the preferred embodiment, a linear, differential transducer 48 is used to measure movement of the external piston. In the transducer, mechanical displacements are converted to electrical signals, which are subsequently amplified and converted to a properly calibrated display of probe displacement.

Figure 6:
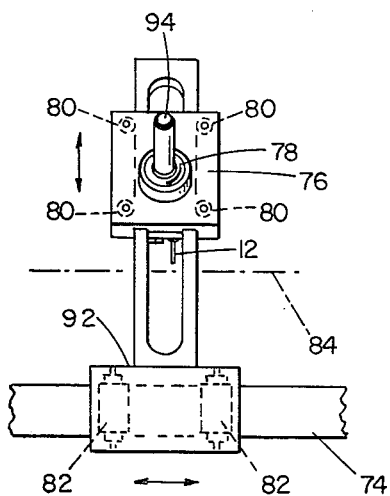
FIG. 6 is an end view of the system and guided mechanical supports.

With reference to FIGS. 3-6, the periodontal probe system is illustrated with a guided mechanical support for automatic or semiautomatic operation. The probe 10, with its gas line 58 and flexible hydraulic tubing 32, is supported in the oral cavity by a probe-support rod 94, which rod is carried by a spherical bearing 78 in the probe carriage 76. The probe carriage 76, in turn, is carried by a guide-rail carriage 92 by means of probe-carriage, needle-bearing rollers 80 (FIG. 6). The guide-rail carriage 92 is similarly carried along the guide rail 74 by a second set of needle-bearing rollers 82. The guide rail 74 lies substantially in or parallel to the patient's bite plane 84. In automated operation, a bite plate 86 is used to provide a fixed frame of reference for aligning the guide rail 74. The bite plate is secured by means of a bite-plate support 88 and a back support 90.

What I claim is:

1. A periodontal apparatus to determine the depth of a periodontal pocket in the oral cavity of a patient, which apparatus comprises in combination:
   (a) a periodontal probe characterized by an elongated element having a tip at the one end thereof for insertion into a periodontal pocket whose depth is to be determined, the tip end having a small passageway therein for the discharge of a fluid therethrough and from the tip of the probe;
   (b) a source of fluid;
   (c) means connecting the source of fluid with the periodontal probe, to permit the flow of fluid, at a constant controlled pressure, from the source to the probe and to permit the fluid to be discharged from the passageway at the probe tip; and
   (d) flow-indicator means to determine the flow rate of the fluid being discharged from the passageway, whereby, on insertion of the probe tip into the periodontal pocket and as the probe tip approaches and contacts the bottom wall of the periodontal pocket, a rapid change in airflow measurement occurs, by means of which change in flow, the depth of the periodontal pocket may be determined.

2. The apparatus of claim 1 wherein said apparatus includes means to introduce the periodontal probe into the periodontal pocket in a force-controlled manner.

3. The apparatus of claim 1 wherein said source of fluid is a source of compressed air.

4. An apparatus for the force-controlled probing of a periodontal pocket in the oral cavity of a patient, which pocket has a bottom wall surface, which apparatus comprises in combination:
   (a) a periodontal probe having a tip at one end for contact with said bottom wall surface of said periodontal pocket, said probe also having an elongated body at the other end adapted to be mounted for slidable movement in a cylinder;
   (b) a cylinder adapted to be placed in said oral cavity, the other end of said probe being slidably mounted in the cylinder for reciprocal movement therein;
   (c) means to effect slidable reciprocal movement of said probe in said cylinder between a reference position and a depth-locating position;
   (d) end-point-determining means for determining the position of said probe tip on reaching said bottom wall surface of said periodontal pocket; and
   (e) depth-measuring means for determining the depth traveled by said probe on reaching said bottom wall surface, whereby the probe tip is moved in a controlled manner to a position adjacent to, or substantially in contact with, said bottom wall surface of said pocket, and wherein the depth of the pocket may be determined.

5. The controlled-probing apparatus of claim 4 wherein the means to effect movement of the periodontal probe within the cylinder comprises:
   (a) a reservoir formed between the elongated body at the other end of the probe and the cylinder;
   (b) an essentially incompressible fluid within the reservoir; and
   (c) fluid-feeding means to apply a controlled pressure to the fluid in the reservoir to move the periodontal probe tip end in a controlled manner within the pocket.

6. The controlled-probing apparatus of claim 5 wherein said fluid-feeding means comprises:
   (a) variable pressure means, external of the periodontal probe and cylinder;
   (b) fluid-connecting means, fluidly connecting the external pressure means with the said reservoir; and
   (c) means to vary the external variable pressure means, whereby changes of pressure in the external, variable pressure means apply a controlled pressure to the fluid in the reservoir and effect slidable movement of the periodontal probe within the cylinder and within said pocket.

7. The controlled-probing apparatus of claim 5 wherein said fluid-feeding means comprises:
   (a) an external piston having a body and a head;
   (b) an external cylinder which receives said piston and characterized by having an inner cylinder wall of such diameter that such external piston is slidably mounted therein, and said wall and said piston head define an external reservoir for storing a variable volume of essentially incompressible fluid;
   (c) displacement means to displace said external piston; and
   (d) fluid-connecting means, fluidly connecting the periodontal-probe reservoir and the external cylinder reservoir.

8. The controlled-probing apparatus of claim 7 wherein said fluid-feeding means further comprises a pressure gauge and a pressure-relief safety valve, both of which are in fluid connection with the fluid-connecting means.

9. The controlled-probing apparatus of claim 7 wherein said displacement means includes an electric motor and gear train.

10. The controlled-probing apparatus of claim 4 wherein the periodontal probe forms part of the end-point-determining means, said end-point determining means comprising:
    (a) the periodontal probe further characterized by an elongated element having said tip at the one end thereof for insertion into a periodontal pocket whose depth is to be determined, the tip end having a small passageway therein for the discharge of a fluid therethrough and from the tip of the probe;
    (b) a source of fluid;
    (c) means connecting the source of fluid with the periodontal probe, to permit the flow of fluid, at a constant controlled pressure, from the source to the probe and to permit the fluid to be discharged from the passageway at the probe tip; and
    (d) flow-indicator means to determine the flow rate of the fluid being discharged from the passageway, whereby, on insertion of the probe tip into the periodontal pocket and as the probe tip approaches and contacts the bottom wall surface of the periodontal pocket, a rapid change in airflow measurement occurs, by means of which change in flow, the depth of the periodontal pocket may be determined.

11. The controlled-probing apparatus of claim 4 wherein said depth-measuring means includes:
    (a) a linear, differential transducer connected to the probe for movement therewith to convert the movement of said probe into an electrical signal proportional to the movement;
    (b) an amplifier which receives the electrical signal from the transducer to amplify the electrical signal;
    (c) a digital converter electrically connected to the amplifier to convert the amplified electrical signal to digital form; and
    (d) an indicator which receives the digital electrical signal from the converter for displaying in digital form the extent of movement of the periodontal probe.

12. An apparatus for force-controlled probing of a periodontal pocket in the oral cavity of a patient, said pocket having a bottom wall surface, and for determining the depth of said pocket, which apparatus comprises:
    (a) a periodontal probe characterized by an elongated element having a tip at one end thereof for insertion into a periodontal pocket whose depth is to be determined, the tip end having a small gas passageway therein for the discharge of gas therethrough and from the tip of the probe, said elongated element also forming a piston having a body and a head;
    (b) a source of gas at a constant pressure;
    (c) means connecting the source of gas with the periodontal probe to permit the flow of gas from the gas source to the probe and the gas to be discharged from the probe tip;
    (d) flow-indicator means to measure the flow rate of the gas being discharged from the probe tip, whereby, on insertion of the probe tip into the periodontal pocket and as the probe tip approaches the bottom wall surface of the periodontal pocket, a rapid change in airflow measurement occurs, by means of which change in flow, the depth of the periodontal pocket may be determined, without penetration of the bottom wall surface of the periodontal pocket by the probe;
    (e) a first cylinder adapted to be placed in said cavity, the piston of said probe being slidably mounted in the cylinder for reciprocal movement therein, the piston head and the cylinder walls defining a first fluid reservoir therebetween for the storage of a first variable volume of essentially incompressible fluid;
    (f) a second piston and cylinder assembly, said second piston having a head and body and being slidably mounted within said second cylinder between a reference position and a locating position, the cylinder walls and piston head forming a second reservoir for the storage of a second variable volume of essentially incompressible fluid;
    (g) an essentially incompressible fluid initially stored within said first and second reservoirs;

(h) connecting means to connect fluid in said first reservoir with fluid in said second reservoir and to allow the transport of fluid therebetween;

(i) means to drive said second piston and cylinder assembly to effect pressurized fluid transport between said first and second reservoirs; and (j) depth-determining means to determine the distance traveled by said probe, said depth-determining means further comprising (i) a transducer means to convert the displacement of the second piston between the reference position and the locating position into an electrical signal proportional to the displacement, (ii) an amplifier electrically connected to the transducer means to amplify the electrical signal received from said transducer, (iii) a data converter electrically connected to the amplifier to convert the amplified electrical signal into digital form, and (iv) a display indicator electrically connected to the converter to display the digital signal from the data converter whereby the displacement of said second piston is shown as a visual display.

13. A removable, replaceable, periodontal probe for use with an hydraulic pressure system to probe a periodontal pocket and with a gas-flow system to determine the location of the bottom surface of the periodontal pocket, which probe comprises:

(a) an elongated body portion having a tip at one end for insertion into said periodontal pocket, the tip end having a small passageway therein for the discharge of fluid therethrough, the body portion also having at or near the other end a connecting means for connection to a source of gas, so as to allow passage of gas through the body portion and from the tip upon connection to a gas-flow system;

(b) a piston-shaped portion including a piston head and piston body connected to the body portion; and (c) a cylindrical housing portion surrounding said piston-shaped portion and permitting the piston-shaped portion to slide therein, the housing portion forming an hydraulic reservoir above the piston head, means for removably connecting said reservoir to the hydraulic-pressure system, whereby pressure from the pressure system upon connection results in movement of the piston-shaped portion and elongated body portion of the probe in the periodontal pocket, and whereby the location of the bottom surface of the pocket can be determined by observed changes in gas flow through the tip.

14. A method of measuring the depth of a periodontal pocket in the oral cavity of a patient without penetration of the bottom wall surface of the periodontal pocket, which method comprises:

(a) inserting a periodontal probe having a tip into the periodontal pocket, while passing a continuous flow of fluid at a predetermined flow rate into the pocket and downwardly through the probe tip; and (b) measuring the fluid flow to determine the point at which a rapid diminution in fluid flow occurs, and, from such change in flow, determining the depth of the periodontal pocket.

15. The method of claim 14 which method further comprises visually displaying the depth of the periodontal pocket in a digital form.

16. The method of claim 14, which method further comprises passing the continuous flow of fluid into the pocket at about 260 ml/minute at about 20–25 psig.

17. The method of claim 14 wherein the fluid passed into the pocket is air.

18. A method of measuring the depth of a periodontal pocket in the oral cavity of a patient, which method comprises:

(a) securing in the patient's oral cavity a cylindrical instrument, which instrument includes a reciprocal, slidably moving, piston-shaped, periodontal probe having a tip and having a gas passageway through said instrument and out said tip;

(b) applying force to said piston-shaped probe to move said probe into the periodontal pocket toward the bottom of the pocket;

(c) passing a continuous flow of gas, at a predetermined flow rate, through the passageway of said probe during its movement into the pocket;

(d) monitoring and measuring the gas flow to determine the point at which a rapid diminution or impediment in gas flow occurs, which serves as an indication of the bottom of the pocket; and (e) determining the distance traveled by said probe in its movement to the bottom of the pocket.

19. The method of claim 18, which method further comprises visually displaying the depth of the periodontal pocket in a digital form.

20. The method of claim 18, which method further comprises passing the continuous flow of gas through the passageway at a flow rate of about 260 ml/minute at about 20–25 psig.

21. The method of claim 18 wherein the gas passed through the passageway is air.

* * * * *